(12) United States Patent
Neff et al.

(10) Patent No.: US 8,785,985 B2
(45) Date of Patent: Jul. 22, 2014

(54) SENSOR FOR DETECTING A COMPONENT OF A GAS MIXTURE

(75) Inventors: Petra Neff, Stuttgart (DE); Alexander Martin, Regensburg (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 13/505,672

(22) PCT Filed: Sep. 20, 2010

(86) PCT No.: PCT/EP2010/063763
§ 371 (c)(1),
(2), (4) Date: Jul. 15, 2012

(87) PCT Pub. No.: WO2011/054577
PCT Pub. Date: May 12, 2011

(65) Prior Publication Data
US 2012/0273846 A1      Nov. 1, 2012

(30) Foreign Application Priority Data
Nov. 3, 2009 (DE) .......................... 10 2009 046 317

(51) Int. Cl.
*G01N 27/403* (2006.01)
(52) U.S. Cl.
USPC ............. 257/253; 257/E29.255; 257/E21.409
(58) Field of Classification Search
USPC ........................... 257/253, E29.255, E21.409
See application file for complete search history.

(56) References Cited

U.S. PATENT DOCUMENTS

| 5,698,771 A | 12/1997 | Shields et al. |
| 2005/0097941 A1* | 5/2005 | Sandvik et al. .............. 73/31.06 |
| 2008/0149571 A1* | 6/2008 | Zeller et al. .................. 210/767 |

FOREIGN PATENT DOCUMENTS

| DE | 29 18 932 A1 | 11/1979 |
| DE | 199 16 798 A1 | 11/2000 |
| DE | 102 45 614 A1 | 5/2003 |
| DE | 10 2004 047 797 A1 | 4/2005 |
| DE | 10 2005 033 639 A1 | 1/2007 |
| DE | 10 2007 040 726 A1 | 3/2009 |
| DE | 10 2009 000 820 A1 | 8/2010 |
| KR | 10-2006-0008496 | 1/2006 |

OTHER PUBLICATIONS

International Search Report corresponding to PCT Application No. PCT/EP2010/063763, mailed Oct. 13, 2010 (German and English language document) (8 pages).

\* cited by examiner

*Primary Examiner* — Timor Karimy
(74) *Attorney, Agent, or Firm* — Maginot, Moore & Beck

(57) ABSTRACT

A sensor for detecting a first component in a gas mixture is disclosed having a gas-sensitive electrode and a catalyst which is arranged on and/or spaced apart from the electrode in a porous carrier ceramic. The catalyst has the effect that a second component in the gas mixture is chemically altered such that the component contributes to no substantial change in the potential of the electrode.

6 Claims, 3 Drawing Sheets

SENSOR FOR DETECTING A COMPONENT OF A GAS MIXTURE

This application is a 35 U.S.C. §371 National Stage Application of PCT/EP2010/063763, filed on Sep. 20, 2010, which claims the benefit of priority to Serial No. DE 10 2009 046 317.8, filed on Nov. 3, 2009 in Germany, the disclosures of which are incorporated herein by reference in their entirety.

BACKGROUND

The present disclosure relates to a sensor for detecting at least a first medium in a media mixture comprising at least the first medium and a second medium, to a method for producing the sensor and to a chip having the sensor.

For example, sensors in the form of field effect transistors are used, inter alia, to determine gas components in gas mixtures. In this case, a gate electrode of the field effect transistor, for example, is sensitive to the gas components to be determined, thus resulting in a change in the potential of the gate electrode. A resultant change in the current flow between a source electrode and a drain electrode of the field effect transistor is associated with the concentration of a gas component. Such sensors are referred to as ChemFETs. Such ChemFETs are used, in particular in exhaust gas lines of internal combustion engines, to measure, for example, the proportion of nitrogen oxide (referred to as $NO_x$ below) in the exhaust gas, as described in DE 10 2007 040 726 A1.

SUMMARY

The sensor according to the disclosure, the method according to the disclosure, and the chip according to the disclosure provide the advantage over conventional solutions that the catalyst whose coefficient of thermal expansion generally differs from that of the electrode is arranged at a distance from the electrode on and/or in the fully porous carrier ceramic, and no thermal strain therefore results between the catalyst and the electrode when the latter are exposed to highly varying temperatures, as is typically the case in the exhaust gas line of an internal combustion engine. In addition, the catalyst adheres comparatively well to the porous carrier ceramic on account of the high surface roughness of the latter. Furthermore, a catalytic activity of the electrode is not influenced by the catalyst on account of the distance, thus improving the measurement accuracy of the sensor.

Advantageous developments and improvements are also disclosed below.

BRIEF DESCRIPTION OF THE DRAWINGS

Exemplary embodiments of the disclosure are illustrated in the drawing and are explained in more detail in the following description.

In the drawing.

DETAILED DESCRIPTION

In the figures, identical reference symbols denote identical or functionally identical elements, unless stated otherwise.

Figure 1:
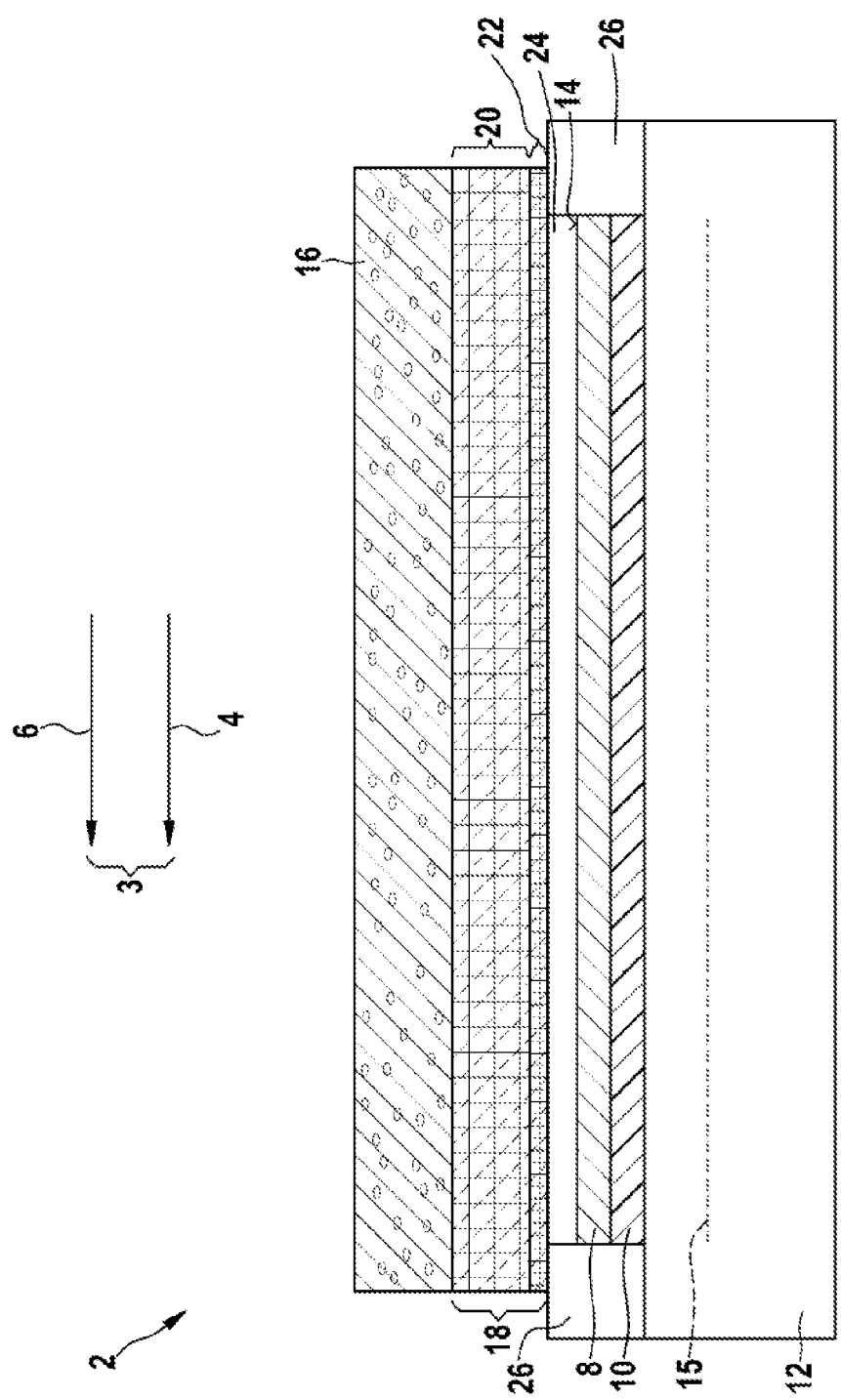
FIG. 1 shows a sectional view of a sensor according to one exemplary embodiment of the disclosure.

FIG. 1 shows a sectional view of a sensor 2 according to one exemplary embodiment of the disclosure.

According to the exemplary embodiment, the sensor 2 is arranged in or adjacent to an exhaust gas stream 3 in an exhaust gas line (not illustrated any further) of an internal combustion engine.

The exhaust gas stream 3 has a media mixture comprising a first medium 4 and a second medium 6. According to the exemplary embodiment, the first medium is $NO_x$ gas and the second medium 6 is hydrocarbon gas. It goes without saying that the exhaust gas stream 3 may also contain yet further media.

The sensor 2 is intended to be used to detect the $NO_x$ gas 4 in the exhaust gas stream 3. In the present case, the term "detect" is used to mean both the pure detection of the presence of $NO_x$ gas 4 in the exhaust gas stream and preferably the measurement of the quantity of the $NO_x$ gas 4. For this purpose, the sensor 2 according to this exemplary embodiment is designed as follows:

The sensor 2 is, for example, in the form of a ChemFET and has a gate electrode 8 which is in contact with a semiconductor substrate 12 via an insulation layer 10.

The semiconductor substrate 12 may be formed from gallium nitride, aluminum nitride, gallium-aluminum nitride or silicon carbide. According to this exemplary embodiment, it is in the form of silicon carbide.

The gate electrode 8 is preferably formed from an oxidation-stable noble metal such as platinum, palladium, gold, iridium, rhenium, rhodium or mixtures thereof and/or from admixture of element compounds of base metals such as hafnium, tantalum and/or aluminum.

The gate electrode 8 may also have a porous coating 14 made of a noble metal or from a noble metal/metal oxide mixed material. The material for the porous coating 14 is preferably selected from the transition elements such as hafnium, tantalum, niobium, tantalum, molybdenum, rhodium, platinum, palladium, silver, gold or mixtures thereof. Electrically conductive compounds such as nitrides, carbides or silicides of the transition elements, for example tungsten or tantalum silicide, are also possible. Cermets which, in addition to said transition elements or their carbides or silicides, have a ceramic component, for example aluminum oxide, silicon dioxide, zirconium dioxide, rare earth metals, such as, in particular, magnesium oxide, are particularly suitable as the noble metal/metal oxide mixed material.

The electrode 8 preferably comprising the porous coating 14 is set up to change its electrical potential if it comes into contact with the $NO_x$ gas 4 or the hydrocarbon gas 6 in the exhaust gas stream 3 or both gases. In addition to the gate electrode 8, the sensor 2 has source and drain electrodes (not illustrated), a change in the electrical potential of the gate electrode 8 changing a current in a channel region 15 in the semiconductor substrate 12 between the source and drain electrodes. The change in the current is evaluated in an evaluation unit (not illustrated) in order to determine which medium is present and the quantity in which this medium is present at the electrode 8.

However, since only the $NO_x$ gas is intended to be detected according to the exemplary embodiment, a catalyst 16 is arranged between the electrode 8 and the exhaust gas stream 3. The catalyst 16 is used to eliminate individual gas components in the exhaust gas stream 3 to which the electrode 8 has an undesirable cross-sensitivity. In this case, the catalyst 16 converts these undesirable gas components into gas components which do not impede a measurement of the gas component to be determined. Therefore, according to the present exemplary embodiment, the catalyst 16 is in the form of an oxidation catalyst which oxidizes the hydrocarbon gas 6 to form carbon dioxide and water. The catalytic oxidation process preferably predominantly takes place at a temperature of the exhaust gas stream 3 in the range between 100 and 650°, preferably between 250 and 550°. The reaction products of carbon dioxide and water do not have a substantial influence on the electrical potential of the electrode 8. In contrast, the $NO_x$ gas 4 can pass unimpeded through the oxidation catalyst 16 to the electrode 8 where it contributes to a change in the electrical potential of the latter.

According to the exemplary embodiment, the catalyst 16 is in the form of a multiplicity of particles each having a ceramic core, for example made of aluminum oxide or zirconium oxide, which has a catalytic sheath, in particular made of noble metal such as platinum, rhodium, palladium, iridium or mixtures thereof. Alternatively, the catalyst 16 itself may be in the form of a porous layer, in particular made of one of the abovementioned noble metals.

According to the exemplary embodiment, the catalyst 16 is partially arranged on, that is to say on the exhaust gas stream side, and partially inside a fully porous carrier ceramic 18 which is in the form of a layer and is itself arranged between the electrode 8 and the exhaust gas stream 3. The carrier ceramic 18 preferably consists of silicon or silicon carbide. In a region 20 on the exhaust gas stream side, the carrier ceramic 18 has pores which have a first diameter of preferably between 2 and 20 μm and in which the catalyst 16 in the form of particles is accommodated. The carrier ceramic also has an electrode-side region 22 which is designed with pores having a second diameter of approximately 0.2-2 μm or less. The catalyst 16 cannot pass into these pores or through these pores with the second diameter, with the result that the catalyst particles 16 cannot come into contact with the electrode 8 in an unwanted manner and cannot fall through the carrier ceramic 18.

Alternatively, the catalyst 16 may also be in the form of a porous layer which is arranged on the carrier ceramic 18.

According to the exemplary embodiment, the carrier ceramic 18 is arranged at a distance from the electrode 8 by means of a gap 24. This avoids the carrier ceramic 18 and the electrode 8 directly touching, thus avoiding strain between them, for example on account of different coefficients of thermal expansion.

The sensor 2 also has a passivation 26 which, together with the catalyst 16, the carrier ceramic 18 and the semiconductor substrate 12, surrounds the electrode 8. The passivation 26 is gastight and is preferably formed from silicon dioxide and/or silicon nitride.

The semiconductor substrate 12 and the carrier ceramic 18 are advantageously formed from the same material or from different materials with substantially the same coefficients of thermal expansion. For example, the semiconductor substrate 12 and the carrier ceramic 18 are preferably both formed from silicon carbide. This makes it possible to avoid strains between the carrier ceramic 18 and the semiconductor substrate 12; a large force flux is thus avoided by the component passivation 26. The component passivation 26 and the insulation layer 10 are so thin (FIG. 1 does not illustrate the size proportions realistically) that they are not relevant to strain between the components of the sensor 2.

A method for producing the sensor 2 according to the exemplary embodiment shown in FIG. 1 is explained in more detail below.

The semiconductor substrate 12 is first of all provided and the insulation layer 10 is applied to the latter.

The electrode 8 is then applied to the insulation layer 10. A passivation 26 is applied to the semiconductor substrate 12 before or after the application of the insulation layer 10 or the electrode 8.

In a further step, a protective layer, for example a protective photoresist, is applied to the electrode 8. The carrier ceramic 18 is then produced, in particular deposited, on the protective layer. The carrier ceramic 18 is deposited, for example, in such a manner that it has the continuous pores already described above. On the other hand, it is also possible to first of all produce the carrier ceramic 18 on the protective layer and then to produce the pores in the carrier ceramic 18.

In a further step, the catalyst 16 is applied to the carrier ceramic 18 and is at least partially introduced into the latter.

According to an exemplary embodiment which is not illustrated, the catalyst 16 may be applied to the carrier ceramic 18 on the exhaust gas stream side as a separate layer. However, according to the present exemplary embodiment, the catalyst 16 is applied to the carrier ceramic 18 in the form of particles already described above and is introduced into the exhaust gas stream side region 20 of the carrier ceramic 18. This may be effected by dipping the carrier ceramic 18 into a suspension of the catalyst 16 or by spraying such a suspension onto the carrier ceramic 18 or else by printing a catalyst paste onto the carrier ceramic 18 in a screen printing method. All of these methods have the feature in common that a certain proportion of the catalyst particles 16 is embedded in the pores of the exhaust gas stream side region 20 of the carrier ceramic 18. As a result of the fact that the pores in the region 22 have a smaller diameter than the catalyst particles 16, the catalyst particles 16 are prevented from being able to pass to the protective layer or subsequently to the electrode 8.

In a further step, the arrangement consisting at least of the catalyst 16 and the carrier ceramic 18 is heat-treated or sintered in order to increase the adhesion between the catalyst 16 and the carrier ceramic 18. Such a heat treatment may be effected, for example, at a temperature of between approximately 200 and 600°.

It is also conceivable to first of all produce the carrier ceramic 18 and to coat it with the catalyst 16 and to heat-treat or sinter the arrangement produced in this manner, if necessary. In a further step, this arrangement could be applied to a further arrangement consisting at least of the semiconductor substrate 12, the insulation layer 10 and the electrode 8.

After the application of the catalyst 16 or preferably after the heat treatment, sintering or porification of the carrier ceramic 18, the protective layer is removed, with the result that the free gap 24 is produced between the carrier ceramic 18 and the electrode 8.

There are various possibilities for removing the protective layer. The common feature of these possibilities is intended to be the fact that the protective layer is removed from the gap 24 through the pores in the carrier ceramic 18.

If the protective layer is in the form of a protective resist, the latter can be removed by means of an organic solvent in which the protective resist is readily soluble. For this purpose, the organic solvent is supplied, through the pores in the carrier ceramic 18, to the protective layer which thus dissolves and is washed out through the pores. According to another variant, the protective layer can be removed by thermal heating, the protective layer first of all being thermally decomposed and then evaporating through the pores in the carrier ceramic 18. For this method, it is favorable if the protective layer is formed from a thermally decomposable photopolymer.

According to an advantageous exemplary embodiment, the protective layer is removed from the gap 24 using the same heat treatment and the adhesion between the catalyst 16 and the carrier ceramic 18 is simultaneously increased. This dispenses with the separate heat treatment of the catalyst 16 together with the carrier ceramic 18, as described above, thus simplifying the method for producing the sensor 2 overall.

Figure 2:
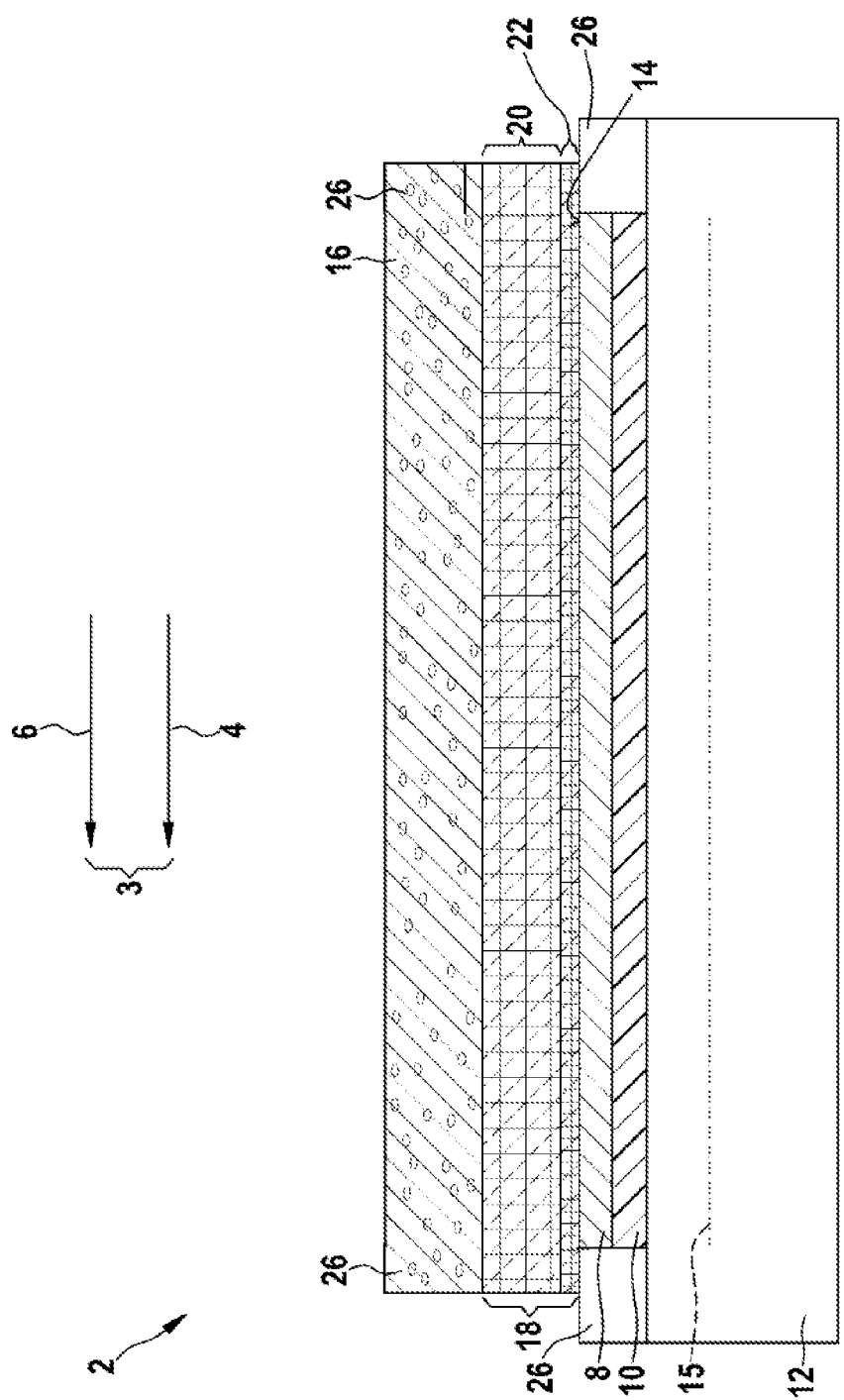
FIG. 2 shows a sectional view of a sensor according to a further exemplary embodiment of the disclosure.

The sensor 2 according to the exemplary embodiment shown in FIG. 2 differs from that shown in FIG. 1 only by virtue of the fact that, in the exemplary embodiment shown in FIG. 2, the carrier ceramic 18 is directly applied to the electrode 8 which comprises the coating 14 if necessary. Therefore, the method step, which was described above in connection with FIG. 1 and according to which the protective layer is applied to the electrode 8 and is subsequently removed again, is dispensed with in the method for producing the sensor 2 according to the exemplary embodiment shown in FIG. 2. For the rest, the described methods for producing the sensor according to FIG. 1 and the sensor 2 according to FIG. 2 are identical.

Figure 3:
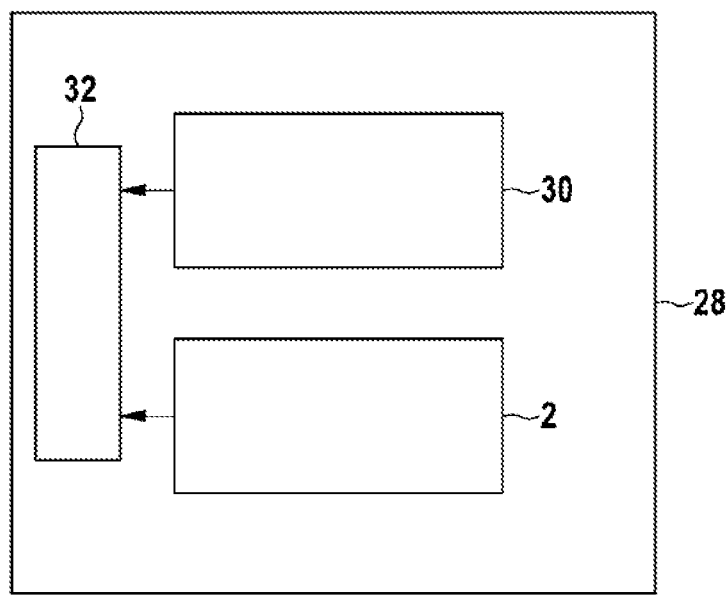
FIG. 3 shows a plan view of a chip according to one exemplary embodiment of the disclosure.

FIG. 3 shows a plan view of a chip 28 having the sensor 2 according to the exemplary embodiment shown in FIG. 1 or 2. The chip 28 also has a further sensor 30. The further sensor 30 is a conventional ChemFET and has an electrode (not illustrated) which is set up to change its potential if it comes into contact with the first medium 4, for example nitrogen oxide gas, and/or the second medium 6, for example hydrocarbon gas. The further sensor 30 according to the exemplary embodiment shown in FIG. 3 does not have a catalyst or the like which would be suitable for changing the second medium 6 in such a manner that the latter substantially does not contribute to changing the potential of the electrode of the further sensor 30. The further sensor 30 does not have, in particular, a catalyst which would be suitable for converting hydrocarbon gas into carbon dioxide and water. The further sensor 30 is thus set up to detect the first and second media 4; 6.

The sensor 2 will therefore produce a measured value for the first medium 4, while the further sensor 30 will produce a measured value for the first and second media 4 and 6.

The chip 28 can now have an evaluation unit 32 which is coupled, for signaling purposes, to the sensors 2 and 30, indicated by the lines with the arrow tips in FIG. 3, the evaluation unit 32 being set up to also determine the proportion of the second medium, that is to say the hydrocarbon gas for example, in the exhaust gas stream 3 from the abovementioned measured values from the sensor 2 and from the further sensor 30.

Although the disclosure was specifically described using exemplary embodiments, it is not restricted thereto but rather can be modified in various ways.

The invention claimed is:

1. A sensor for detecting at least a first medium in a media mixture comprising at least the first medium and a second medium, the sensor comprising:
    an electrode configured to change its potential if it comes into contact with at least one of the first medium and the second medium; and
    a catalyst configured to chemically change the second medium in the media mixture in such a manner that the second medium does not contribute to a substantial change in the potential of the electrode if the media mixture comes into contact with the electrode;
    wherein the catalyst is arranged at a distance from the electrode on and/or in a fully porous carrier ceramic.

2. The sensor as claimed in claim 1, wherein the carrier ceramic includes one of silicon and silicon carbide.

3. The sensor as claimed in claim 1, wherein the pores in an electrode-side region of the carrier ceramic each possess a diameter of between 0.2 and 2 micrometers.

4. The sensor as claimed in claim 1, wherein the carrier ceramic is positioned at a distance from the electrode so as to define a gap.

5. The sensor as claimed in claim 1, wherein the carrier ceramic is directly applied to the electrode, and/or the electrode is applied to a substrate, which is made of a material having approximately the same coefficient of thermal expansion as the material of the carrier ceramic, by way of an insulation layer.

6. A chip, comprising:
    a sensor configured to detect at least a first medium in a media mixture comprising at least the first medium and a second medium, the sensor including (i) an electrode configured to change its potential if it comes into contact with at least one of the first medium and the second medium, and (ii) a catalyst configured to chemically change the second medium in the media mixture in such a manner that the second medium does not contribute to a substantial change in the potential of the electrode if the media mixture comes into contact with the electrode,
    wherein the catalyst is arranged at a distance from the electrode on and/or in a fully porous carrier ceramic.

* * * * *